United States Patent [19]

Thinnes

[11] 4,327,732
[45] May 4, 1982

[54] INCONTINENT PAD
[75] Inventor: Joel H. Thinnes, Three Oakes, Mich.
[73] Assignee: Weyerhaeuser Company, Tacoma, Wash.
[21] Appl. No.: 166,923
[22] Filed: Jul. 8, 1980
[51] Int. Cl.³ .............................................. A61F 5/44
[52] U.S. Cl. .................................. 128/290 R; 128/295
[58] Field of Search .............. 128/284, 286, 287, 289, 128/290 R, 295, 296

[56] References Cited
U.S. PATENT DOCUMENTS

| | | | |
|---|---|---|---|
| 2,831,486 | 4/1958 | Sanders | 128/289 |
| 3,094,990 | 6/1963 | Neilson | 128/289 |
| 4,067,336 | 1/1978 | Johnson | 128/284 |

Primary Examiner—C. Fred Rosenbaum
Attorney, Agent, or Firm—Townsend and Townsend

[57] ABSTRACT

An incontinent pad is disclosed that is of paddle-like shape and includes a main body section terminating in a front section having a curved outer periphery foldably attached thereto and a pair of overhanging members secured to opposite sides of the main body section. The pad includes a plurality of layers of moisture absorbing material. In use, the outer sections are folded relative to the wearer to fit against the inward portions of the upper thighs of the wearer of the pad. A backing sheet of moisture repelling material is provided to overlie the absorbent layers.

3 Claims, 2 Drawing Figures

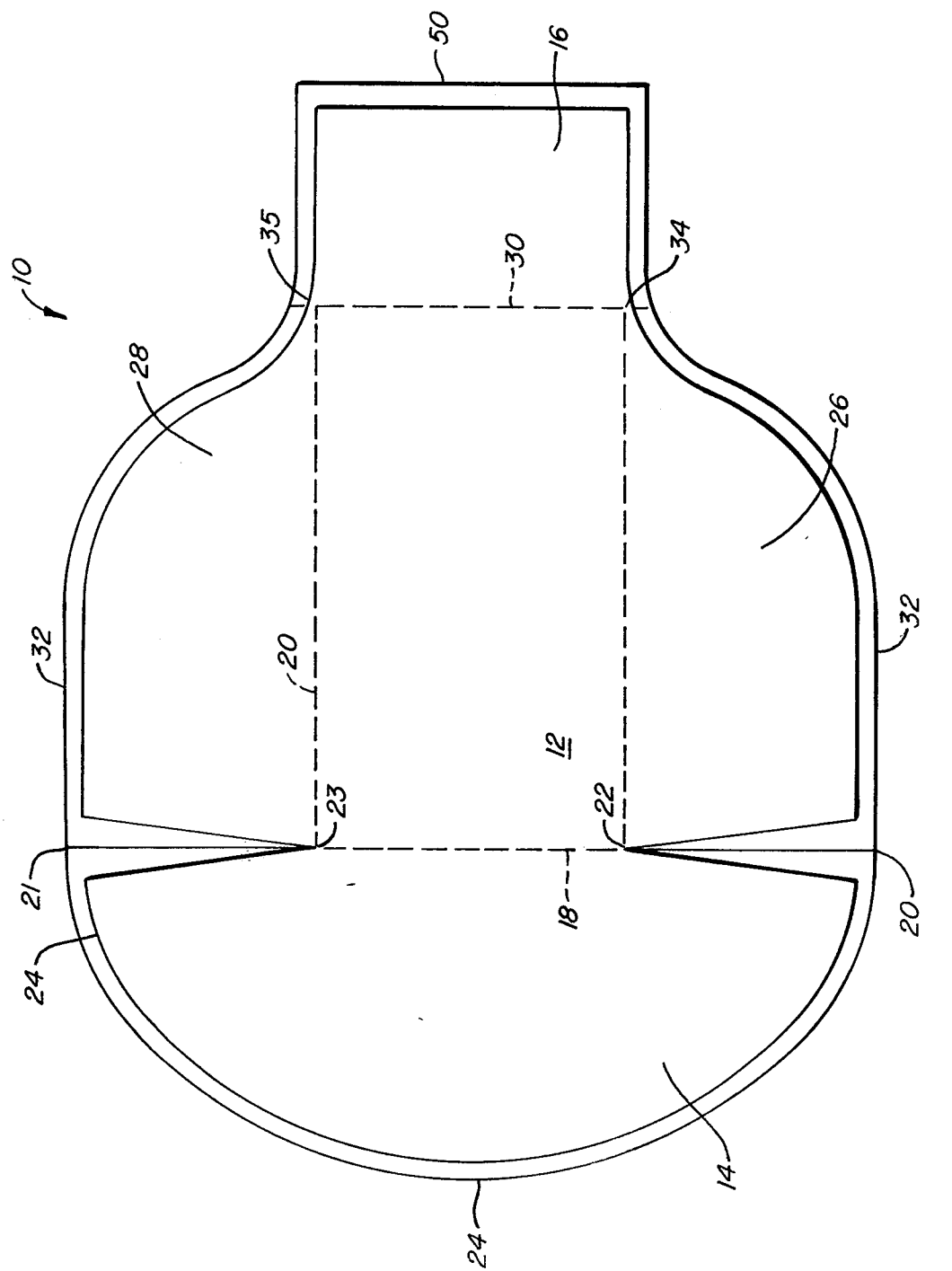

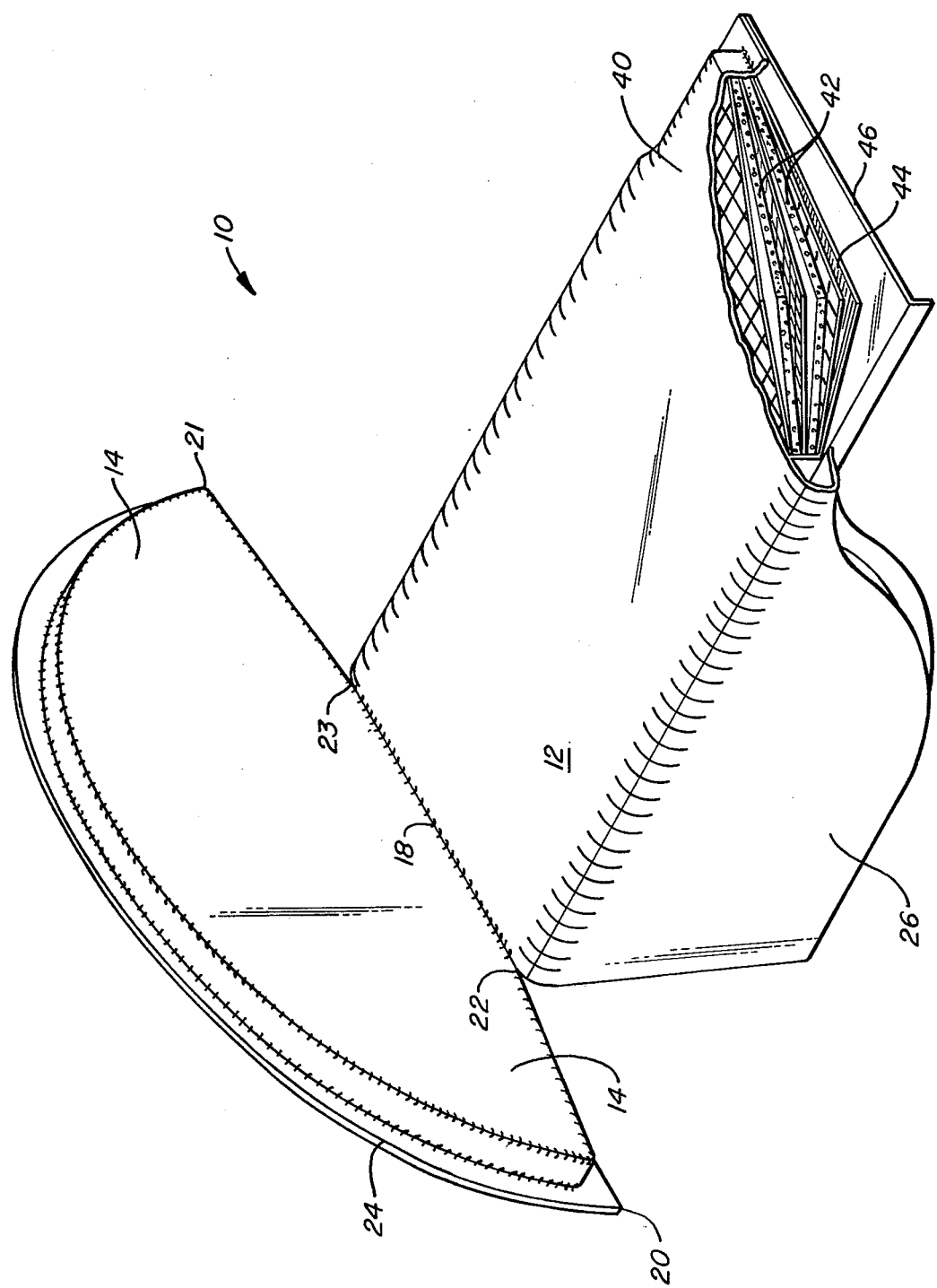
FIG._2.

INCONTINENT PAD

This invention relates to an incontinent pad adapted to be worn by either a hospitalized patient or by one who is ambulatory and who endeavors to overcome the difficulties occasioned when the excretory powers of an individual patient are lost.

Many people, those who are older in particular, become incontinent and thus require some external appendage to care for the conditions where there is a loss, or at least a temporary loss, of the ability to control the normal body processes. Such help is achieved by the present invention which provides the wearer of the unit herein to be described with some degree of assurance that existing problems are recognized and made much easier to bear.

The purposes of this invention can be most readily appreciated when it is seen that the problem can be handled to a great extent by the use of a pad which has both moisture absorbing and repelling properties by which the discomfort can be minimized. The invention is constituted essentially of a wrap-around surface, including an internal shield or pad that will protect the wearer from a failure to achieve complete control of this habits. In particular, the invention results from the use of a combination of sheets of material that have moisture absorbing properties. These sheets are assembled into a pad also having moisture repellant or holding properties and held within a binder or the equivalent. The assembly is adapted to be wrapped about the patient who is then effectively encased in the unit which is folded relative to him.

The invention overcomes many of the disadvantages and inconveniences of prior art assemblies which include many and various types of diapers, pads, and various forms of pants that are offered for like purposes. The present invention also has the advantage of utilizing a pad formed of material, such as a wood pulp sheet, which acts to filter and absorb waste material but which can still be used with little or no discomfort.

It is, therefore, an object of the present invention to provide an improved form of incontinent pad which is completely sanitary and which can be used for long periods of time.

A further object is that of providing a pad which is of comfort to the wearer and which will offer no binding effect upon him, and which, if the patient is non-ambulatory will offer negligible resistance to motion.

The foregoing objects and others will become readily apparent upon reading the following detailed description of a preferred embodiment thereof as further illustrated in the attached drawings, in which:

FIG. 1 is a general plan view of a preferred form of pad unit; and

FIG. 2 is essentially a partial perspective view showing the manner of folding the various parts thereof prior to the use thereof, and which also shows generally the manner by which several pads of differing forms may be assembled so that the various components are set in substantial sandwich form.

While the drawings depict one particular way by which the invention may be assembled, it shall nonetheless be considered only as an illustration of one preferred form. It is intended that these specifications be given the broadest meaning possible in the light of what is herein set forth.

The pad 10 of FIG. 1 may be formed of any suitable soft fabric, such as a fibrous moisture absorbing sheet or a flannel-like material, or any other suitable form of material, such as cotton or the like.

In the preferred embodiment, complete pad 10 is formed into a paddle-like shape within which there is secured a sandwich-like liner, later to be described herein, which is a combination of moisture absorbing materials and sheets that form a barrier to moisture. The contour of the structure consists of three main sections, including main body 12 having forward section 14 which is curved outwardly, and rear section 16 formed generally as a flattened strip. The several sections are preferrably cut or stamped from a single sheet of material as a backing. So considered, pad 10 is formed, cut or stamped with a forward section 14, the main body section or the central section 12, and the rear section 16.

Forward section 14 is adapted to fold along axis 18 against the body of the wearer, along a forward edge of central section 12. Fold 18 extends between the points 20 and 21 laterally of the unit 10 to points 22 and 23. To provide for this folding, section 14 is slit relative to the main body or central section 12 along the path 20 to 22, and also from point 21 to 23. This forward section 14 is formed with a curved outer edge 24 which extends from the body at point 20 to point 21. The purpose for this will be later explained.

Next, the main or central body section 12 is provided with a pair of folded flap or overhanging sections 26 and 28 which are opposite each other and extend outwardly from the axis about which forward section 14 is adapted to fold to a rear axis 30 which extends from the inner edge of the central section 12 to the rearmost section 16 having rear edge 50 and which is generally parallel to the axis 18. The edge 24 of forward section 14 mates with a similar edge 32 at approximately points 20 and 21 and continues to points 34 and 35 where the axis 30 is cut, as indicated by the dash lines on the drawing, to provide for movement and folding of the sections 26 and 28 about axes from between points 23,24 and points 23,35, respectively. This axis of fold is essentially normal to the fold axis 22,23 and permits the overhanging portions 26 and 28 to be folded downwardly relative to the main body section 12, for a purpose later to be explained.

Lastly, the end section 16 can be folded about a rear fold axis 30, as desired, to a position next to the wearer's body.

With the several parts having been described, it is apparent that there is basis for the inclusion of the moisture absorbing material within the outer pad supporting structure as a whole. For this purpose, referring to FIG. 2, the pad structure comprises a series of smaller pads which form a sandwich of sheets for absorbing moisture from the patient to protect him from the effects thereof. So considered, the laminae, as used, comprises generally an outer sheet of embossed moisture absorbing material 40 which forms an overlap to a sheet of pulp (such as wood pulp) 42, and over this there is usually a similar sheet of super absorbent tissue laminate 44. These sheets are normally all fastened together in any suitable manner and then the combination is backed by a polyethylene backing sheet 46.

When assembled into a unit of the general form of FIG. 2, the product is ready for use. A unit of the form where the moisture absorbing pad of FIG. 2 is secured on the strip of FIG. 1 within the confines of the member 16 so as to extend from the forward part thereof and to the axis 18 rearwardly to approach the rear end 50. So positioned, the various components can be appropriately fastened, as by sewing, stapling or by any other means desired, to outer edge 24,32 or an edge within the confines of the unit as a whole.

In preparing for use, the complete pad is placed between the legs of a wearer in such fashion that the rounded forward component 12 is forward. Being so placed, the part is folded upwardly and bent back about the axis 18 until it comes to bear against the body of the wearer. In being so bent backward the outer forward member 14 retains its curved status.

The overhanging portions 26 adjacent to the central portion 12 which respectively extend outwardly from the outside members 32 so that the parts between points 22 and 34 (and between points 23 and 35) are folded downwardly relative to the central section, as illustrated by FIG. 2. When the pad is put to use, the downwardly depending overhanging portions 26 and 28 are folded generally adjacent to the thighs of the wearer's right and left legs and are adapted to be fastened there by the use of adhesives, tapes or the like.

The overhanging rear section 16 extends between the legs of the wearer and when folded about the axis of fold 30 and turned upwardly, will fit against the wearer's back.

Thus, the pad generally encases the wearer by the front section 14 folding upwardly to the body, by depending members 26 and 28 folded outwardly and downwardly for fitting about the patient's inner thigh section of each leg, by section 16 folding upwardly along the patient's back, and by central unfolded section 12 fitting between the legs of the patient. The patient is thus essentially provided with a covering which fully surrounds him at all times.

Other and various modifications may readily be made and the unit may be designed to fit closely to different size individuals. The backing sheet 46 which covers the complete unit is a polyethylene sheet through which no moisture can pass. Such a backing sheet also has the advantage of offering practically no friction to the bed sheets in case the wearer is a bed patient, so that movement in the bed and between the sheets is not restricted.

Having now described the invention, what is claimed is:

1. An incontinent pad adapted to be worn between the legs of a subject for protection purposes, comprising a member having a forward curved section and an attached rearward section formed as a strip-like member, the sections being adapted to merge along a transverse axis of fold, said sections then forming a paddle-like section at their axes of merger with the forward section then being formed as a sector-shaped section having a rearward portion starting at the axis of fold forming a main body section of strip-like shape extending outwardly therefrom with the forward section then forming a forward body section, the forward body section having its forward portion adapted to be folded close to the body of a wearer upon being folded from the merging axis with the main body section, the said main body section having a width at the axis of merger which substantially corresponds to that of the forward section at said axis of merger, the formed wider sections of the main body member being adapted to be turned upon an axis at substantially a right angle to the axis of merger with the forward section so that it may be turned inwardly about its axis of fold so as to be adjacent the inner side of the left and right legs of a wearer, the said folded portion then being secured to the said inner side of the legs of the wearer to hold any moisture externally developed within the pad to the inner side adjacent to the legs of the wearer, a channel member formed upon the said main body member from its under side, a plurality of sandwiched moisture maintaining strips removably supported within said channel and adapted to contain any moisture developed therein from escaping, a channel covering sheet of moisture retaining character covering the removable strips within the said channel section and held to cover all of the removable strips therein, and means to fold the rear extended end of said supported body section about its rear end and that of the channel section so that it may be held against the body of the wearer with all of the moisture within the said removable strips confined therein.

2. The combination claimed in claim 1 wherein the moisture absorbing sheets are formed from a laminated pulp material.

3. The combination claimed in claim 2 where the outer covering sheet is a polyethylene member.

* * * * *